United States Patent [19]

Tracey et al.

[11] Patent Number: 6,117,837

[45] Date of Patent: Sep. 12, 2000

[54] INHIBITING PROINFLAMMATORY CYTOKINE PRODUCTION

[75] Inventors: Kevin J. Tracey, Greenwich, Conn.; Haichao Wang, Avenel, N.J.

[73] Assignee: The Picower Institute for Medical Research, Manhasset, N.Y.

[21] Appl. No.: 09/476,919

[22] Filed: Jan. 4, 2000

Related U.S. Application Data

[62] Division of application No. 08/932,871, Sep. 18, 1997, Pat. No. 6,011,005.

[51] Int. Cl.[7] .......................... A01N 37/18; A61K 38/00; A61K 38/16; C07K 1/00

[52] U.S. Cl. ..................................... 514/2; 514/8; 514/12; 514/21; 530/350; 530/324

[58] Field of Search ................. 514/2, 8, 12, 21; 230/324, 350

[56] References Cited

U.S. PATENT DOCUMENTS 6,011,005   1/2000   Tracey et al. ................. 514/2

OTHER PUBLICATIONS

Nelen et al., *Lancet*, vol. 350, Sep. 20, 1997, pp 861–862.

*Primary Examiner*—Avis M. Davenport
*Attorney, Agent, or Firm*—Davis Wright Tremaine LLP

[57] ABSTRACT

There is disclosed a method for helping to prevent miscarriages during pregnancy, comprising administering an effective amount of a fetuin polypeptide.

2 Claims, 1 Drawing Sheet

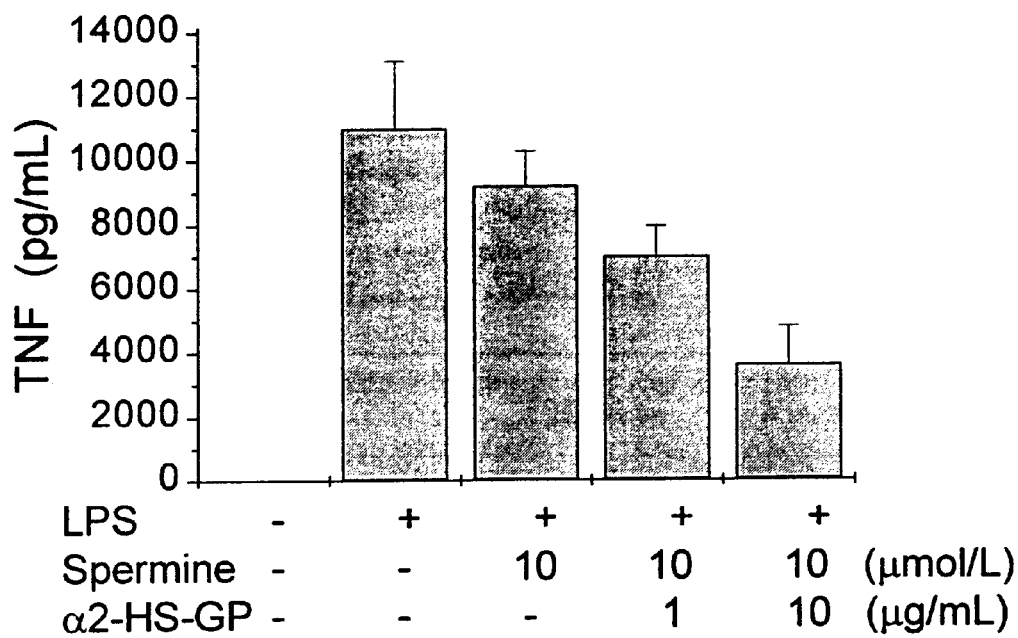
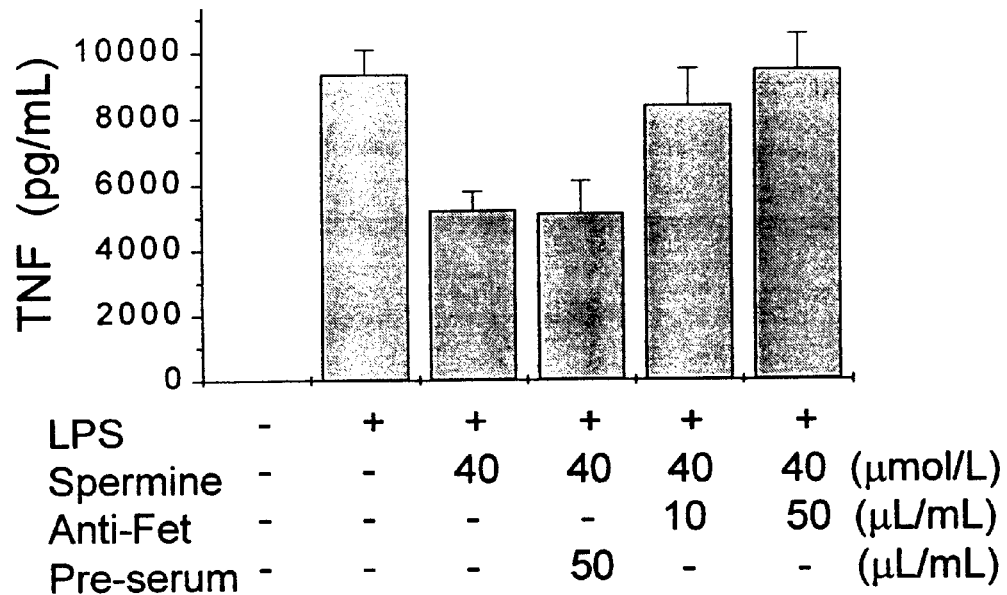

INHIBITING PROINFLAMMATORY CYTOKINE PRODUCTION

CROSS REFERENCE TO RELATED APPLICATION

The present patent application is a divisional of U.S. patent application Ser. No. 08/932,871 filed Sep. 18, 1997 now U.S. Pat. No. 6,011,005.

TECHNICAL FIELD OF THE INVENTION

The present invention provides a method for prevention of miscarriages during pregnancy.

BACKGROUND OF THE INVENTION

Pregnancy has been termed "Nature's transplant" because the developing fetus, essentially a foreign tissue graft, is protected from rejection by its host, the mother (Editorial: "Nature's transplant" *Lancet* 1:345–346, 1974). Rejection of a transplanted allograft in an immunocompetent host is normally mediated by the macrophage-derived cytokine tumor necrosis factor (TNF) (Eason et al., *Transplantation* 59:300–305, 1995). Excessive production of TNF during pregnancy causes spontaneous abortion (Shaarawy et al., *Acta Obstet. Gynecol. Scand.* 76:205–211, 1997; and Mallmann et al., *Arch. Gynecol. Obstet.* 249:73–78, 1991). Recently, spermine, a ubiquitous biogenic amine present in large amounts in the amnion, has been shown to counter-regulate the immune response by inhibiting the production of TNF and other pro-inflammatory cytokines by human mononuclear cells (Zhang et al., *J Exp. Med.* 185:1759–1768, 1997).

Fetuin is a globular 341-amino acid protein containing 20–25% carbohydrate (by weight) and 6 internal disulfide bonds. The human fetuin sequence (also known as α2-HS glycoprotein) is provided herein as SEQ ID NO. 1 and SEQ ID NO. 2. Fetuin was first identified over 50 years ago as a major protein component of bovine fetal serum but its biological function remains unclear. Bovine fetuin is a globular 341 amino acid polypeptide with six internal disulfide bonds and three N-linked and two O-linked oligosaccharide chains. Primary amino acid sequence and the position of cysteine residues are well conserved in human, bovine, sheep, rat and mouse fetuin homologs (Dziegielewska et al., *J Biol. Chem.* 265:4354, 1990; Rauth et al., *Eur. J Biochem.* 205:321,1992; Lee et al., *Proc. Natl. Acad. Sci. USA* 84:4403, 1987; and Brown et al., *Eur. J Biochem.* 205:321, 1992). Fetuin levels in human plasma are regulated in the manner of a negative acute phase reactant (Lebreton et al., *J Clin. Invest.* 64:1118, 1979). IL-1 was shown to suppress fetuin transcript levels in cultured hepatocytes (Akhoundi et al., *J Biol. Chem.* 268:15925, 1994). Fetuin appears to be expressed in bone because transcripts have been detected in both chondrocytes and osteoblasts (Yang et al., *Blood* 12:7, 1991). The polypeptide α2-HS glycoprotein is a human homolog of fetuin and is secreted in high levels by adult liver into the peripheral circulation (Triffitt et al., *Nature* 262:226, 1976).

Human fetuin has 3 N-linked oligosaccharide chains (attached to the amine nitrogen atom of asparagine), and 2 O-linked oligosaccharide chains (attached to the oxygen atom of serine or threonine). The sugar moiety directly attached to the fetuin polypeptide is usually a N-acetylglucosamine residue. The terminal sugar residue is usually a sialic acid, in particular a N-acetylneuraminic acid (NANA) residue, which bears a net negative charge. If one removes the terminal sialic acid residue from fetuin by neuraminidase treatment, the resulting glycoprotein is an asialofetuin. Fetuin is also a carrier protein for growth factors. Fetuin is sometimes referred to as α2-HS-glycoprotein. Thus, it is considered that fetuin's biological effects on cultured cells are related to its carrier function for molecules with growth-promoting properties.

The synthesis of human α2-HS-glycoprotein is down-regulated by cytokines (hIL-1β, hIL-6) (Lebreton et al., *J Clin. Invest.* 64:1118–1129, 1979). Human fetuin levels are decreased (25–50%) in trauma patients (van Oss et al., *J Trauma* 15:451, 1975). Therefore, there is a need in the art to find a utility for fetuin and to understand fetuin's physiological role and the importance of its many negatively charged (at physiologic pH) sialic acid residues.

SUMMARY OF THE INVENTION

The present invention provides a method for helping to prevent miscarriages and pre-term labor during pregnancy, comprising administering an effective amount of a fetuin polypeptide. Preferably, the human fetuin polypeptide has a primary sequence according to SEQ ID NO. 1 or SEQ ID NO. 2 or a shortened fragment thereof having at least 250 amino acid residues.

BRIEF DESCRIPTION OF THE DRAWING

FIG. 1 shows the suppression of TNF secretion by spermine in the presence of fetuin (FIG.1A) or fetuin-specific polyclonal antibodies (FIG. 1B). HuPBMCs or RAW 264.7 cells were stimulated with *E. coli* endotoxin (LPS, 100 ng/ml) in the presence of spermine, human fetuin (α2-HS-glycoprotein), or polyclonal antibodies against fetuin. TNF levels in supernatants four hours post-LPS stimulation were determined by ELISA as previously described (Zhang et al., *J Exp. Med.* 185:1759–1768, 1997). Note that fetuin increases the TNF-suppressing activity of spermine, and anti-fetuin renders normal LPS-stimulated macrophages refractory to this suppression. A Student's t-test was performed and a $P<0.05$ was considered significantly different (*).

DETAILED DESCRIPTION OF THE INVENTION

The present invention is based upon the new discovery that a fetal plasma glycoprotein, fetuin, is required for the inhibition of TNF production by spermine. Although fetuin was first described more than fifty years ago in fetal bovine serum, and subsequently found to share high homology to human fetuin (α2-HS-glycoprotein), its role in pregnancy and fetal development, until now, has been unknown. While investigating the mechanism underlying spermine-mediated suppression of TNF production in the murine macrophage-like cell line, RAW 264.7, we came upon the surprising discovery that macrophages lost their responsivity to spermine when cultured under low serum conditions. That is, despite the addition of cytokine-suppressing concentrations of spermine to these cells, the production of TNF was uninhibited by spermine after LPS stimulation.

It has previously been proposed that fetuin can function as a carrier of cell-modulating agents. We next showed that fetuin binds spermine by measuring the concentration of spermine after fractionation of a fetuin/spermine mixture (0–20 μM fetuin/100 μM spermine) via ultrafiltration. These results revealed that one molecule of fetuin is capable of binding 4–6 molecules of spermine. Since spermine and fetuin levels are both extremely high in the fetus and amnion, it now appears that they are ideally poised to counter-regulate TNF production in pregnancy.

EXAMPLE 1

This example illustrates the identification of fetuin as the protein responsible for some of the spermine-based activity observed in macrophage cultures. We added fractionated proteins from normal cells and assayed for their ability to restore the spermine-dependent inhibition of TNF production under serum-free culture conditions, because we hypothesized that these "spermine-non-responsive cells" had become deprived of a protein that was required to inhibit the production of TNF. After anion-exchange chromatography and SDS-PAGE gel elution, we isolated a single protein that mediated the responsivity of macrophage cultures to spermine. Computer-based protein database analysis of the N-terminal amino acid sequence identified this protein as fetuin.

The role of fetuin as a mediator of spermine inhibition of TNF production was confirmed by adding highly purified fetuin (Sigma, St. Louis, Mo.), together with spermine, to LPS-stimulated human peripheral blood mononuclear cells (HuPBMCs). As shown in FIG 1A, the level of TNF produced by LPS-stimulated HuPBMCs was significantly reduced by increasing the concentrations of fetuin for a given dose of spermine. Fetuin alone had no effect on TNF production (data not shown), indicating that both spermine and fetuin were required for the suppression of TNF synthesis.

We prepared polyclonal antiserum against purified fetuin, using standard techniques. The anti-fetuin polyclonal antibodies abrogated spermine-mediated suppression of TNF production from LPS-stimulated macrophages, whereas the control (pre-immune) serum did not (FIG. 1B). These data show that fetuin is required for spermine to suppress TNF production in normal human monocytes.

We claim:

1. A method for inhibiting pro-inflammatory cytokine production under conditions where extracellular spermine levels are elevated, comprising administering an effective amount of a human fetuin polypeptide.

2. The method of claim 1 wherein the human fetuin polypeptide has a primary sequence according to SEQ ID NO. 1 or SEQ ID NO. 2, or a shortened fragment thereof having at least 250 amino acid residues.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 359 amino acids
      (B) TYPE: amino acid
      (C) STRANDEDNESS: single
      (D) TOPOLOGY: linear (ii) MOLECULE TYPE: protein (iii) HYPOTHETICAL: no (iv) ANTI-SENSE: no (v) FRAGMENT TYPE: N-terminal fragment (vi) ORIGINAL SOURCE:
      (A) ORGANISM: human (xi) SEQUENCE DESCRIPTION: SEQ ID NO: 1:

```
Met Lys Ser Phe Val Leu Leu Phe Cys Leu Ala Gln Leu Trp Gly
                 5                  10                  15

Cys His Ser Ile Pro Leu Asp Pro Val Ala Gly Tyr Lys Glu Pro
                20                  25                  30

Ala Cys Asp Asp Pro Asp Thr Glu Gln Ala Ala Leu Ala Ala Val
                35                  40                  45

Asp Tyr Ile Asn Lys His Leu Pro Arg Gly Tyr Lys His Thr Leu
                50                  55                  60

Asn Gln Ile Asp Ser Val Lys Val Trp Pro Arg Arg Pro Thr Gly
                65                  70                  75

Glu Val Tyr Asp Ile Glu Ile Asp Thr Leu Glu Thr Thr Cys His
                80                  85                  90

Val Leu Asp Pro Thr Pro Leu Ala Asn Cys Ser Val Arg Gln Gln
                95                 100                 105

Thr Gln His Ala Val Glu Gly Asp Cys Asp Ile His Val Leu Lys
               110                 115                 120

Gln Asp Gly Gln Phe Ser Val Leu Phe Thr Lys Cys Asp Ser Ser
               125                 130                 135
```

```
Pro Asp Ser Ala Glu Asp Val Arg Lys Leu Cys Pro Asp Cys Pro
                140                 145                 150

Leu Leu Ala Pro Leu Asn Asp Ser Arg Val Val His Ala Val Glu
                155                 160                 165

Val Ala Leu Ala Thr Phe Asn Ala Glu Ser Asn Gly Ser Tyr Leu
                170                 175                 180

Gln Leu Val Glu Ile Ser Arg Ala Gln Phe Val Pro Leu Pro Val
                185                 190                 195

Ser Val Ser Val Glu Phe Ala Val Ala Ala Thr Asp Cys Ile Ala
                200                 205                 210

Lys Glu Val Val Asp Pro Thr Lys Cys Asn Leu Leu Ala Glu Lys
                215                 220                 225

Gln Tyr Gly Phe Cys Lys Gly Ser Val Ile Gln Lys Ala Leu Gly
                230                 235                 240

Gly Glu Asp Val Arg Val Thr Cys Thr Leu Phe Gln Thr Gln Pro
                245                 250                 255

Val Ile Pro Gln Pro Gln Pro Asp Gly Ala Glu Ala Glu Ala Pro
                260                 265                 270

Ser Ala Val Pro Asp Ala Ala Gly Pro Thr Pro Ser Ala Ala Gly
                275                 280                 285

Pro Pro Val Ala Ser Val Val Gly Pro Ser Val Val Ala Val
                290                 295                 300

Pro Leu Pro Leu His Arg Ala His Tyr Asp Leu Arg His Thr Phe
                305                 310                 315

Ser Gly Val Ala Ser Val Glu Ser Ser Ser Gly Glu Ala Phe His
                320                 325                 330

Val Gly Lys Thr Pro Ile Val Gly Gln Pro Ser Ile Pro Gly Gly
                335                 340                 345

Pro Val Arg Leu Cys Pro Gly Arg Ile Arg Tyr Phe Lys Ile
                350                 355                 359

(2) INFORMATION FOR SEQ ID NO: 2:

(i) SEQUENCE CHARACTERISTICS:
        (A) LENGTH: 367 amino acids
        (B) TYPE: amino acid
        (C) STRANDEDNESS: single
        (D) TOPOLOGY: linear (ii) MOLECULE TYPE: protein (iii) HYPOTHETICAL: no (iv) ANTI-SENSE: no (v) FRAGMENT TYPE: N-terminal fragment (vi) ORIGINAL SOURCE:
        (A) ORGANISM: human (xi) SEQUENCE DESCRIPTION: SEQ ID NO: 2:

Met Lys Ser Leu Val Leu Leu Leu Cys Leu Ala Gln Leu Trp Gly
                 5                  10                  15

Cys His Ser Ala Pro His Gly Pro Gly Leu Ile Tyr Arg Gln Pro
                20                  25                  30

Asn Cys Asp Asp Pro Glu Thr Glu Glu Ala Ala Leu Val Ala Ile
                35                  40                  45

Asp Tyr Ile Asn Gln Asn Leu Pro Trp Gly Tyr Lys His Thr Leu
                50                  55                  60
```

```
Asn Gln Ile Asp Glu Val Lys Val Trp Pro Gln Gln Pro Ser Gly
                65              70              75

Glu Leu Phe Glu Ile Glu Ile Asp Thr Leu Glu Thr Thr Cys His
                80              85              90

Val Leu Asp Pro Thr Pro Val Ala Arg Cys Ser Val Arg Gln Leu
                95              100             105

Lys Glu His Ala Val Glu Gly Asp Cys Asp Phe Gln Leu Leu Lys
                110             115             120

Leu Asp Gly Lys Phe Ser Val Val Tyr Ala Lys Cys Asp Ser Ser
                125             130             135

Pro Asp Ser Ala Glu Asp Val Arg Lys Val Cys Gln Asp Cys Pro
                140             145             150

Leu Leu Ala Pro Leu Asn Asp Thr Arg Val Val His Ala Ala Lys
                155             160             165

Ala Ala Leu Ala Ala Phe Asn Ala Gln Asn Asn Gly Ser Asn Phe
                170             175             180

Gln Leu Glu Glu Ile Ser Arg Ala Gln Leu Val Pro Leu Pro Pro
                185             190             195

Ser Thr Tyr Val Glu Phe Thr Val Ser Gly Thr Asp Cys Val Ala
                200             205             210

Lys Glu Ala Thr Glu Ala Ala Lys Cys Asn Leu Leu Ala Glu Lys
                215             220             225

Gln Tyr Gly Phe Cys Lys Ala Thr Leu Ser Glu Lys Leu Gly Gly
                230             235             240

Ala Glu Val Ala Val Thr Cys Thr Val Phe Gln Thr Gln Pro Val
                245             250             255

Thr Ser Gln Pro Gln Pro Glu Gly Ala Asn Glu Ala Val Pro Thr
                260             265             270

Pro Val Val Asp Pro Asp Ala Pro Pro Ser Pro Pro Leu Gly Ala
                275             280             285

Pro Gly Leu Pro Pro Ala Gly Ser Pro Pro Asp Ser His Val Leu
                290             295             300

Leu Ala Ala Pro Pro Gly His Gln Leu His Arg Ala His Tyr Asp
                305             310             315

Leu Arg His Thr Phe Met Gly Val Val Ser Leu Gly Ser Pro Ser
                320             325             330

Gly Glu Val Ser His Pro Arg Lys Thr Arg Thr Val Val Gln Pro
                335             340             345

Ser Val Gly Ala Ala Ala Gly Pro Val Val Pro Pro Cys Pro Gly
                350             355             360

Arg Ile Arg His Phe Lys Val
                365     367
```